United States Patent [19]
Alexander

[11] Patent Number: 6,035,705
[45] Date of Patent: Mar. 14, 2000

[54] METHOD FOR CHARACTERIZATION OF FUELS

[75] Inventor: William R. Alexander, Huntington, W. Va.

[73] Assignee: Marathon Ashland Petroleum LLC

[21] Appl. No.: 09/144,790

[22] Filed: Sep. 1, 1998

[51] Int. Cl.$^7$ .......................... G01N 11/00; G01N 21/00; G01N 21/85

[52] U.S. Cl. ........................ 73/61.48; 73/61.43; 250/576; 436/172

[58] Field of Search .......................... 73/38, 61.41, 61.43, 73/61.44, 61.48; 250/576; 436/172

[56] References Cited

U.S. PATENT DOCUMENTS

| | | |
|---|---|---|
| 3,899,688 | 8/1975 | Péirères ..................................... 250/576 |
| 4,489,593 | 12/1984 | Pieters et al. ................................ 73/38 |
| 4,929,049 | 5/1990 | Le Goullon et al. . |
| 5,026,139 | 6/1991 | Klainer et al. . |
| 5,069,061 | 12/1991 | Sell et al. ................................ 73/19.01 |
| 5,098,659 | 3/1992 | Yim et al. . |
| 5,153,931 | 10/1992 | Buchanan et al. . |
| 5,165,005 | 11/1992 | Klainer et al. . |
| 5,244,813 | 9/1993 | Walt et al. ................................ 436/172 |
| 5,253,037 | 10/1993 | Klainer et al. . |
| 5,349,181 | 9/1994 | Saini et al. . |
| 5,563,707 | 10/1996 | Prass et al. . |
| 5,567,622 | 10/1996 | Juduszliwer et al. . |
| 5,583,049 | 12/1996 | Altman et al. . |

*Primary Examiner*—Hezron Williams
*Assistant Examiner*—Jay L. Politzer
*Attorney, Agent, or Firm*—Albert J. Adamcik; Richard D. Stone

[57] ABSTRACT

In a principal embodiment, the invention relates to a method in which a water sample containing dissolved hydrocarbon fuel to be identified is contacted with a fiber optic element adapted to adsorb a hydrocarbon fuel on at least a portion of the element, for a time sufficient to adsorb a characterizing amount of the fuel from the water sample. The fiber optic element containing adsorbed hydrocarbon fuel is then removed from the water sample, and then at least the portion of the fiber optic element containing adsorbed fuel is immersed in or surrounded with water. The adsorbed hydrocarbon fuel is allowed to desorb from the fiber optic element while the rate of desorption of the fuel from the fiber optic element is measured by a fiber optic chemical sensor system of which the fiber optic element is a part. The set of values derived from the concentration measurements together identify or characterize the hydrocarbon fuel, and may further be represented mathematically by a desorption ratio value which is characteristic of the fuel.

23 Claims, 3 Drawing Sheets

METHOD FOR CHARACTERIZATION OF FUELS

FIELD OF THE INVENTION

The invention relates generally to a method for identifying or characterizing fuels, especially those dissolved in water, utilizing a fiber optic chemical sensor. The invention particularly concerns the identification of diesel fuel or gasoline in water.

BACKGROUND OF THE INVENTION

Prior to the invention, fiber optic chemical sensor systems have been used to measure the total amount of hydrocarbon dissolved in water. Such systems find useful application in field operations, since the systems can be made portable. Commercial fiber optic chemical sensor systems generally comprise a fiber optic element, a source of light providing light through the core of the element, a detector for sensing changes in the light transmitted through the fiber optic element and for generation of signals, and an analyzer for the signals, the analyzer normally comprising of a computer and appropriate software for processing the signals. At least some of the systems rely on proprietary claddings or coatings on the optic fiber which produce a controlled leakage of light which is a function of the refractive index of the surrounding medium. In one such fiber optic chemical sensor system, a fluorescent tip formed of a fluorescent dye immobilized on the tip of the fiber is provided, an excitation signal is transmitted through the fiber to the tip, and the fluorescent emission is detected through the fiber. In a second type of sensor system, a reflective tip is formed at the end of the fiber so that incident light is transmitted back. In yet a third group, the light source and the detector are positioned at opposite ends of the optic fiber so that variations of the intensity of the light transmitted through the core are detected.

However, as those skilled in the art are aware, the analysis of dissolved hydrocarbon is complicated by the reality that each species of hydrocarbon has its own specific response factor. For this reason, until recently, as indicated in U.S. Pat. No. 5,026,139, fiber optic chemical sensor systems have been generally limited to a single chemical species or physical parameter. Thus, while measurement of total hydrocarbon content in water with such systems has been achieved with a reasonable degree of accuracy, speciation or definition between classes of mixtures with the systems has proven more difficult. Accordingly, prior to the invention, fiber optic chemical sensor technology relied substantially on either thorough knowledge of the source of the water sample, or on additional analytical techniques, generally requiring laboratory facilities, e.g., gas chromatography, to determine hydrocarbon species or a class of hydrocarbons dissolved in water. There has therefore existed a particular need for a technique for differentiating among fuel types dissolved in water, particularly a procedure or method readily adapted for use in a field environment. The invention addresses this need.

SUMMARY OF THE INVENTION

Accordingly, in one embodiment, the invention relates to a process or method comprising providing a water sample containing dissolved hydrocarbon fuel to be identified, immersing in, or contacting the water sample with, a fiber optic element of a fiber optic chemical sensor system, the fiber optic element selected being adapted to adsorb (and, as further described, desorb) a hydrocarbon fuel on at least a portion of the element, for a time sufficient to adsorb at least a characterizing or differentiating amount of the fuel from the water sample. The fiber optic element or probe containing adsorbed hydrocarbon fuel is then removed from the water sample, and then at least a portion of the fiber optic element containing a characterizing amount or more of adsorbed fuel is immersed in or surrounded with water. The adsorbed hydrocarbon fuel is desorbed or allowed to desorb from the fiber optic element, and the rate of desorption of the fuel from the fiber optic element is measured by the fiber optic chemical sensor system of which the fiber optic element is a part. As used herein, the phrase "fiber optic element" refers to an optic fiber or waveguide which guides light by internal reflection and is adapted for chemical sensing, while the phrase "fiber optic chemical sensor system" is taken to refer to operatively associated elements including, but not limited to, a light source, a fiber optic element (generally coated or cladded, as known in the art), a detector for light transmitted through the core of the fiber optic element, capable of generating signals, and an analyzer for the signals, as more fully described hereinafter, the system being useful for or designed for determining the concentration of hydrocarbon constituents in water. According to the invention, the rate of desorption of the hydrocarbon fuel, or of the components thereof, may be determined by the fiber optic chemical sensor system by taking a series of concentration measurements, over time, the measurements being accomplished by detection by the detector of changes of light intensity transmitted through the fiber optic element and generation of electrical signals in response thereto, with transmission of the signals generated to the analyzer. The series or set of concentration measurements identifies or characterizes the hydrocarbon fuel, and may further be represented mathematically by a desorption ratio value, discussed more fully hereinafter, which is characteristic of the fuel. Accordingly, upon comparison of the sets of measurements or of the desorption ratios obtained from different fuel-containing water samples, hydrocarbon fuel types are readily differentiated. In a further aspect, a series of samples of known hydrocarbon fuel-water compositions may be prepared, and measurements may be taken of their desorption rates, in the manner of the invention, to establish a dataset of concentration measurements, or of desorption ratios. Concentration measurements of a hydrocarbon fuel type to be identified may then be taken, and its desorption rate, or its desorption ratio, may then be compared with the values in the dataset, or the desorption ratios previously determined, and the composition type of the unknown may then be determined. Again, it is within the scope of the invention to prepare a water sample of an unknown hydrocarbon fuel in water, for measurement as described herein, either for type analysis, or for preparation of a dataset. Finally, the procedure of the invention is also adapted for utilization with standard concentration measurement procedures, since there is a time requirement before measurement of desorption rate to ensure the presence of sufficient adsorbed hydrocarbon fuel on the element or probe. Thus, one or more measurements of the concentration of the hydrocarbon in the water sample may be made before removal of the fiber optic element from the water sample to clean water for the rate of desorption measurement.

DETAILED DESCRIPTION OF THE INVENTION

Figure 1:
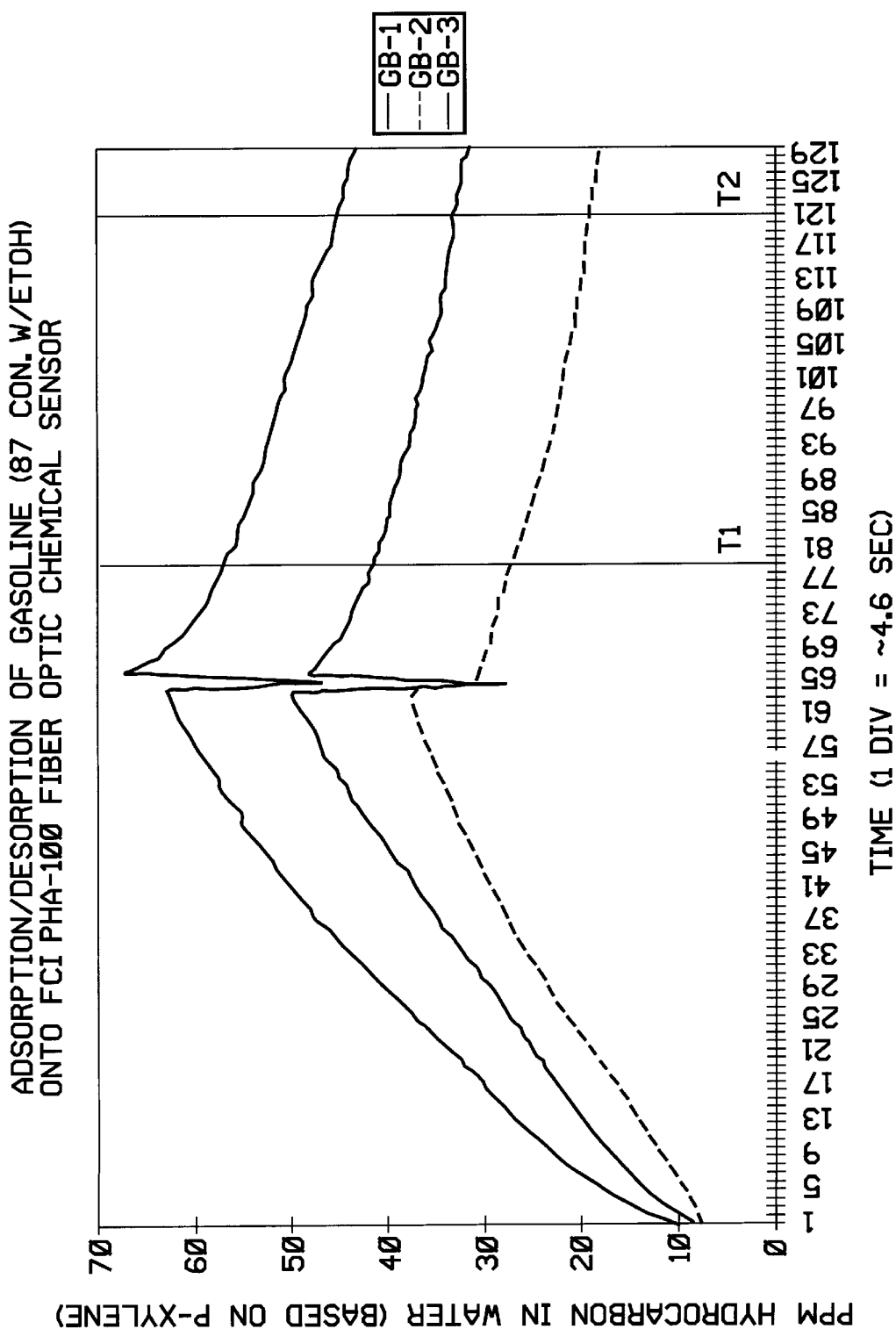
FIG. 1 is a graph depicting the desorption of gasoline in water.

Any common hydrocarbon fuel may be differentiated by the invention, provided the fiber optic element is capable of adsorbing the fuel and permits desorption of a sufficient amount for concentration measurement in water unsaturated by the fuel. As utilized herein, the term "hydrocarbon", with respect to the fuels analyzed, is used in a broad sense to indicate fuels comprised at least principally of carbon and hydrogen, it being recognized, for example, that many petroleum derived fuels contain a variety of compounds which contain other elements, such as sulfur, oxygen, and heavy metals. However, the invention is especially advantageous in differentiating gasoline in water or diesel fuel in water.

The method of the invention will be carried out under suitable conditions of temperature and pressure. In view of the nature of hydrocarbon fuels and the requirements of adsorption from and desorption in water, ordinary atmospheric conditions, such as might be encountered in the field, are preferred. A sufficient amount of the hydrocarbon fuel must be adsorbed on the probe or element and desorb, as indicated, to allow concentration measurements, i.e., at least a characterizing amount or an amount sufficient to differentiate the hydrocarbon fuel must adsorb and subsequently desorb. Since this amount will vary with the hydrocarbon fuel type, precise ranges cannot be given, but concentrations as low as 10 to 300 ppm are measurable by typical fiber optic chemical sensor systems and will provide concentration data sets. Normally, given a fiber optic element capable of adsorbing the fuel, adsorption of a characterizing amount will generally be accomplished simply by immersing sufficient area or portion of the fiber optic element which is adapted to adsorb the hydrocarbon fuel in the fuel-water mixture for a time sufficient to adsorb the necessary or characterizing amount. This time and surface area may be determined by ordinary experimentation, particularly in light of the experimental procedures detailed more fully hereinafter.

The particular fiber optic element and fiber optic chemical sensor system employed are matters of choice, with the exception of the requirement for capability of adsorption of the hydrocarbon fuel and desorption of the required amount of the hydrocarbon fuel in water, and per se form no part of the present invention. As indicated, the suitability of a particular fiber optic element for adsorption and desorption of hydrocarbon fuel may be determined by routine experimentation. Normally, the common fiber optic elements, or probes, commercially available will be adequate to provide sufficient surface area for the required amount of adsorbed hydrocarbon fuel. In the same manner, the particular overall fiber optic chemical sensor system which will provide the appropriate sensing and analysis may be selected from those commercially available. The chemical sensor systems may also include appropriate temperature sensing means, to the end that temperature variation, such as temperature variation from a calibrating temperature, may be taken into account and concentration measurements be corrected therefor.

In the desorption procedure or step of the invention, water which is at least reasonably or substantially pure is required. As those skilled in the art will recognize, the amount of fuel to be desorbed from the fiber optic element is quite small, and concentrations of impurities which significantly impact refractive index will vitiate results. Normally, de-ionized water will be employed.

As indicated, each hydrocarbon fuel has a characteristic response to light leakage from the fiber optic element. Similarly, it has been determined that each fuel exhibits its own desorption rate from the fiber optic element into the water, and this factor lends itself to the formulation of a value which readily distinguishes the fuel. According to the invention, a time interval of measurement may be selected, starting at a time after the element or probe has been placed in the water, and, depending on the fuel type, when the desorption has become at least substantially linear, e.g., one and a quarter minutes after placement of the fiber optic element or probe in water. Measurements of concentration of the hydrocarbon fuel, using the fiber optic chemical sensor system, may then be taken periodically, and preferably regularly, e.g., every 5 seconds. The time interval (T1–T2) is arbitrary and is selected to allow a sufficient number of measurements for accuracy. The ratio of the PPM measurements at T2 and T1 is then calculated (PPM2/PPM1), as are ratios at T1+1, T1+2, T1+3; and T2+1, T2+2, and T2+3. The ratios generated for each sample are then averaged to reduce the amount of noise in the data. The averaged value is a desorption ratio value which is characteristic of the fuel.

The following experiments illustrate the invention, and were conducted utilizing a PHA-100 PetroSense® Portable Hydrocarbon Analyzer from FCI Environmental, Inc. The PHA-100 analyzer utilizes a fiber optic hydrocarbon sensing probe. A proprietary coating on the optic fiber responds to the presence of increasing or decreasing levels of hydrocarbons, effecting modulations of transmitted light intensity along the fiber which are translated by a detector into variable outputs. These analog signals are then converted to digital signals via an analog to digital converter, and the digital signals are then loaded into the computer of the PHA-100. Once the digital data is in the computer, it can be converted to PPM measurements via calibration equations, which are determined by the standardization procedure which uses p-xylene for calibration. (The calibration equations also include temperature corrections. The temperature of the sample is also read during the measurement via a thermistor which is part of the system located in close proximity to the fiber optic element.) The calculated PPM value is displayed on the front panel of the PHA-100 computer. According to the manufacturer, the unit provides a quantitative measurement of hydrocarbon in water to within 10% by weight. Screening measurement reputedly can be very accurate, but is described as level ore, which requires only a verification that the analyzer is within user established calibration requirements using a quick check of one standard.

In the following experiments, twenty-one separate fuel and water mixtures were prepared by blending the respective fuels, or mixtures thereof, with water. For the experiments, three different gasolines were chosen: a 93 octane conventional with MTBE, an 87 octane conventional with ethanol, and an 87 octane conventional with no oxygenates. Three different diesel fuels were chosen, a low-sulfur diesel and two #2 diesel fuels. Of the twenty-one samples, eighteen were prepared by adding samples of each of these fuel types to 250 ml of de-ionized water, in three different concentrations. Three additional experimental samples were prepared by adding varying amounts of 87 octane conventional gasoline and #2 diesel fuel in 1:1 ratios to 250 ml of de-ionized water. Concentrations of the fuels were varied in order to ascertain if the determination of fuel type according to the invention is independent of hydrocarbon concentration. The total mass amounts of the fuels added to the 250 ml de-ionized water samples varied from 0–0253 g to 0.1027 g. The fuel-water samples thus produced are similar in hydrocarbon content to those which might commonly occur. Care was taken not to supersaturate the de-ionized water with the experimental hydrocarbon during the preparation of the samples. In the course of the experiments, the samples containing diesel fuel developed a sheen on the top of the water. When the probe was removed from the sample container, some of the sheen stuck to the probe and the PPM values became higher as the probe was placed in the clean de-ionized water for the desorption to take place. This occurrence is not unexpected and does not effect the normal operation of the PHA-100 as described in its operating instructions. The correct response factor to use may easily be determined, provided the value of the response factor has already been determined for the specific instrument in use by using standard PHA-100 techniques.

In each experiment, a prepared sample was placed in the sample container provided with the PHA-100, and the probe of the PHA-100 was inserted in the sample. The hydrocarbon molecules of the fuels were allowed to adsorb on the fiber optic element of the probe for five minutes. A concentration measurement was not made. At five minutes, the probe was removed from the sample, and was placed into a sample container containing sufficient de-ionized water to cover the portion of the element having adsorbed hydrocarbon molecules. The hydrocarbon molecules were then allowed to desorb from the de-ionized water, and concentration readings were taken, starting at 6.13 minutes from the beginning of the experiment. (Since the instrument is not able to record dynamic measurements, the instrument was operated in the continuous mode, and concentration readings were taken approximately every 4.6 seconds, for a period of ten minutes, using a stop watch).

Figure 2:
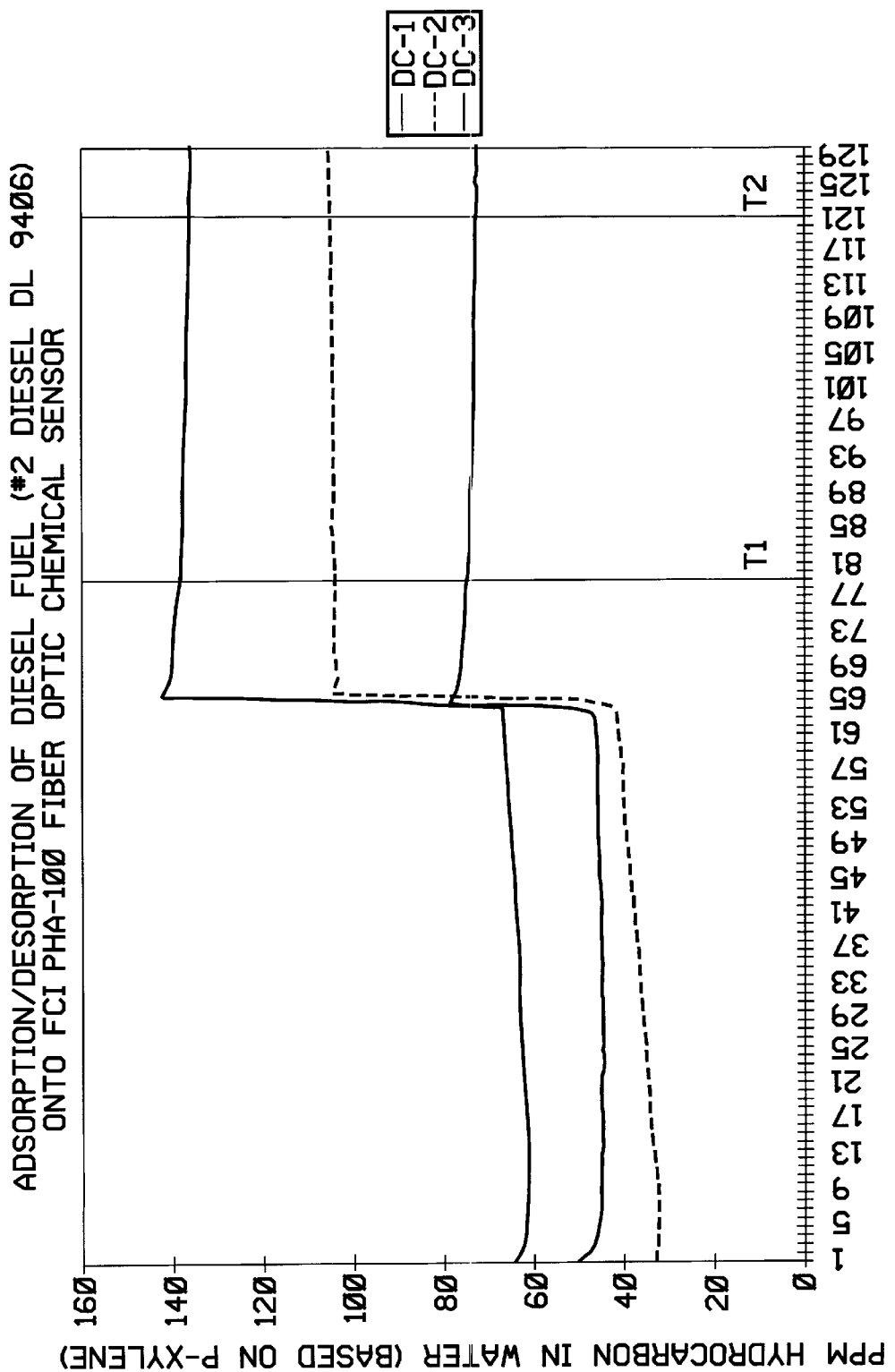
FIG. 2 is a graph depicting the desorption of diesel fuel in water.
Figure 3:
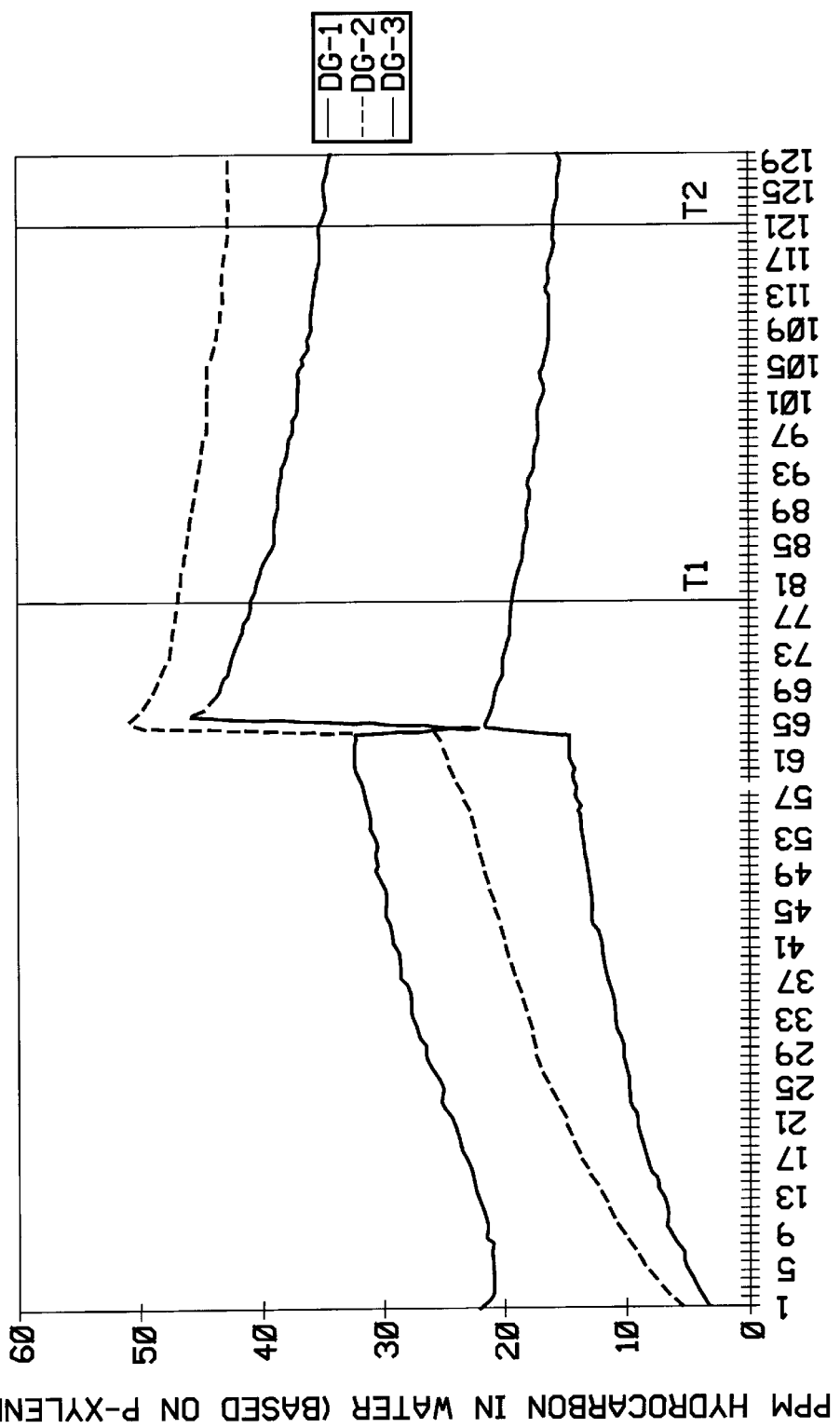
FIG. 3 is a graph depicting the desorption of a 1:1 mixture of diesel and gasoline in water.

As indicated, three different groups of fuel-water mixtures were chosen: gasoline-water, diesel-water, and a 1:1 mixture of gasoline and diesel with water. FIG. 1 illustrates a plot of the concentration measurements of gasoline-water, while FIG. 2 illustrates the results of measurements of a diesel-water mixture. The plots demonstrate clearly the very different desorption characteristics of gasoline and diesel fuel. The plot of FIG. 3 demonstrates the rate of desorption of a 1:1 mixture of gasoline and diesel, the plot illustrating desorption characteristics of both gasoline and diesel.

To evaluate more fully the results of the experiments, the following mathematical processing was conducted. With reference to the Figures, a 3.22 minute time interval, starting at 6.13 minutes into the measurement, was selected. (This time interval corresponds to the period between divisions in the plots marked as 80 and 122, identified as T1 and T2). The ratio of the PPM measurements at T2 and T1 was calculated (PPM2/PPM1), as were ratios at T1+1, T1+2, T1+3; and T2+1, T2+2, and T2+3. The ratios generated for each sample were then averaged to reduce the amount of noise in the data. In addition to the data sets illustrated in the plots, the exercise was repeated with the additional runs mentioned. The results are set forth in the following table.

TABLE

| Gasoline-water | | | |
|---|---|---|---|
| G-1 | G-2 | G-3 | Av. Ratio |
| 0.687262 | 0.821491 | 0.749395 | 0.752716 |
| GB-1 | GB-2 | GB-3 | Av. Ratio |
| 0.799885 | 0.702548 | 0.791421 | 0.764618 |
| GC-1 | GC-2 | GC-3 | Av. Ratio |
| 0.763542 | 0.744221 | 0.739324 | 0.749029 |

Average Gasoline Ratio - 0.755454 ± 0.044111

| Diesel-water | | | |
|---|---|---|---|
| D-1 | D-2 | D-3 | Av. Ratio |
| 0.934838 | 0.853055 | 0.873314 | 0.887069 |
| DB-1 | DB-2 | DB-3 | Av. Ratio |
| 0.912178 | 0.950623 | 0.937663 | 0.933488 |
| DC-1 | DC-2 | DC-3 | Av. Ratio |
| 0.952267 | 0.994701 | 0.972487 | 0.973152 |

Average Diesel Ratio - 0.931236 ± 0.045321

| 1:1 Diesel:Gasoline-water | | | |
|---|---|---|---|
| DG-1 | DG-2 | DG-3 | Av. Ratio |
| 0.81915 | 0.910068 | 0.856351 | 0.861857 ± 0.045709 |

As the table clearly illustrates, the very distinct average desorption ratios provide ready differentiation among the samples.

As indicated, the invention is also adapted to combination with standard fiber optic concentration measurement procedures, since there is a time requirement to ensure sufficient adsorbed fuel before measurement of the desorption rate can begin. Accordingly, one or more measurements of concentration may be made before removal of the fiber optic element containing adsorbed hydrocarbon fuel from the water sample. The invention may thus be utilized to provide both analysis of fuel type and concentration thereof in the water sample.

While the invention has been illustrated with reference to specific equipment and embodiments, it is to be understood that various modifications and embodiments will be suggested to those skilled in the art upon reading and understanding this disclosure. For example, as indicated, the invention contemplates the use of any suitable fiber optic chemical sensor system in addition to the specific unit described in the experiments. Accordingly, it is intended that all such modifications and embodiments be included in the invention and that the scope of the invention be limited only by the appended claims.

What is claimed is:

1. A method comprising contacting a water sample containing dissolved hydrocarbon fuel to be identified with a fiber optic element of a fiber optic chemical sensor system, for a time sufficient to adsorb at least a characterizing amount of the hydrocarbon fuel from the water sample on the fiber optic element; removing said fiber optic element containing the adsorbed fuel from the water sample; surrounding a portion of the fiber optic element containing at least a characterizing amount of adsorbed fuel with water, and allowing a characterizing amount of the adsorbed hydrocarbon fuel to desorb from the fiber optic element into the water and measuring the concentration of desorbed fuel in the water, over time, with the fiber optical chemical sensor system.

2. The method of claim 1 wherein the desorption rate of the hydrocarbon fuel is determined by the concentration measurements over time, the concentration measurements by said system being determined by detection of changes of light intensity transmitted through the fiber optic element to the detector and generation of signals from the detector in response to such changes, transmission of the signals and conversion thereof to digital form, and conversion of the digital signals by computer processing.

3. The method of claim 1 wherein the concentration measurements obtained provide a set which characterizes the hydrocarbon fuel.

4. The method of claim 2 wherein the signals are processed to provide a rate of desorption of the fuel characteristic of the hydrocarbon fuel.

5. The method of claim 3 wherein the set of concentration measurements obtained is compared with that of a different hydrocarbon fuel sample.

6. The method of claim 3 wherein the set of concentration measurements obtained is compared with that of a known hydrocarbon fuel sample.

7. A method comprising blending a hydrocarbon fuel to be identified with water, and obtaining a water sample containing dissolved hydrocarbon fuel to be identified; contacting said water sample with the fiber optic element of a fiber optic chemical sensor system, for a time sufficient to adsorb at least a characterizing amount of said fuel from the water sample on the fiber optic element; removing said fiber optic element containing the adsorbed fuel from the water sample; surrounding a portion of the fiber optic element containing at least a characterizing amount of adsorbed hydrocarbon fuel with water, and allowing a characterizing amount of the adsorbed hydrocarbon fuel to desorb from the fiber optic element into the water while measuring the rate of desorption of the hydrocarbon fuel with the fiber optic chemical sensor system.

8. The method of claim 7 wherein the rate of desorption of the hydrocarbon fuel is compared with that of a different hydrocarbon fuel sample.

9. A method comprising blending a hydrocarbon fuel with water, and obtaining a water sample containing dissolved hydrocarbon fuel; contacting said water sample with a fiber optic element of a fiber optic chemical sensor system, for a time sufficient to adsorb at least a characterizing amount of the fuel from the water sample on the fiber optic element; removing said fiber optic element containing the adsorbed fuel from the water sample; surrounding a portion of the fiber optic element containing at least a characterizing amount of adsorbed hydrocarbon fuel with water, and allowing a characterizing amount of the adsorbed hydrocarbon fuel to desorb from the fiber optic element into the water while measuring the rate of desorption of the fuel from the fiber optic element with the fiber optic chemical sensor system.

10. The method of claim 9 wherein desorption rate is characteristic of the hydrocarbon fuel.

11. The method of claim 10 wherein the hydrocarbon fuel is diesel fuel.

12. The method of claim 11 wherein measured concentration values are processed to provide a rate of desorption characteristic of the diesel fuel.

13. The method of claim 10 wherein measured concentration values are processed to provide rate of desorption characteristic of the gasoline.

14. The method of claim 13 wherein measured concentration values are processed to provide a mathematical ratio of desorption characteristic of the gasoline.

15. A method comprising a water sample containing dissolved hydrocarbon fuel to be identified with a fiber optic element of a fiber optic chemical sensor system, for a time sufficient to adsorb at least a characterizing amount of said hydrocarbon fuel from the water sample on the fiber optic element; removing said fiber optic element containing the adsorbed fuel from the water sample; surrounding a portion of the fiber optic element containing at least a characterizing amount of adsorbed fuel with water, and allowing a characterizing amount of the adsorbed hydrocarbon fuel to desorb from the fiber optic element into the water while measuring the rate of desorption of the hydrocarbon fuel from the fiber optic element by a series of measurements, over time, with the fiber optic chemical sensor system, of concentration of desorbed hydrocarbon fuel.

16. The method of claim 15 wherein desorption rate is characteristic of the hydrocarbon fuel.

17. The method of claim 16 wherein the hydrocarbon fuel is diesel fuel.

18. The method of claim 16 wherein the hydrocarbon fuel is gasoline.

19. A method comprising contacting a water sample containing dissolved hydrocarbon fuel to be identified with a fiber optic element of a fiber optic chemical sensor system, for a time sufficient to adsorb at least a characterizing amount of the fuel from the water sample on the fiber optic element; measuring the concentration of the dissolved hydrocarbon fuel in the water sample; removing said fiber optic element containing the adsorbed fuel from the water sample; surrounding a portion of the fiber optic element containing a characterizing amount of adsorbed fuel with water, and allowing a characterizing amount of the adsorbed hydrocarbon fuel to desorb from the fiber optic element into the water while measuring the rate of desorption of the hydrocarbon fuel from the fiber optic element by a series of measurements, over time, with the fiber optic chemical sensor system, or concentration of desorbed hydrocarbon fuel.

20. A method comprising contacting a eater sample containing dissolved hydrocarbon fuel to be identified with a fiber optic element of a fiber optic chemical sensor system, for a time sufficient to adsorb at least a characterizing amount of the hydrocarbon fuel from the water sample on the fiber optic element; removing said fiber optic element containing the adsorbed fuel from the water sample; surrounding a portion of the fiber optic element containing at least a characterizing amount of adsorbed fuel with water, and desorbing a characterizing amount of the adsorbed hydrocarbon fuel from the fiber optic element into the water and measuring the concentration of desorbed fuel in the water, over time, with the fiber optic chemical sensor system.

21. A method comprising providing a plurality of water samples each containing dissolved hydrocarbon fuel; contacting each water sample with a fiber optic element of a fiber optic chemical sensor system, for a time sufficient to adsorb at least a characterizing amount of said fuel from the water sample on the fiber optic element; with each water sample contacted, removing the fiber optic element containing the adsorbed hydrocarbon fuel from the sample and surrounding a portion of the removed fiber optic element containing at least a characterizing amount of adsorbed fuel with water, and allowing at least a characterizing amount of the adsorbed hydrocarbon fuel to desorb from the fiber optic element into the water, and measuring the concentration of desorbed fuel in the water, over time, with the fiber optic chemical sensor system, and producing a dataset of concentration values, or desorption rates, from said plurality of water samples; contacting a further water sample containing dissolved hydrocarbon fuel to be identified with a fiber optic element of a fiber optic chemical sensor system, for a time sufficient to adsorb at least a characterizing amount of the hydrocarbon fuel to be identified from the water sample on the fiber optic element; removing said fiber optic element containing the adsorbed fuel to be identified from the further water sample; surrounding a portion of the fiber optic element containing at least a characterizing amount of adsorbed fuel to be identified with water, and allowing a characterizing amount of the adsorbed hydrocarbon fuel to be identified to desorb from the fiber optic element into the water and measuring the concentration of desorbed fuel in the water, over time, with the fiber optic chemical sensor system; comparing the concentration values obtained of the hydrocarbon fuel to be identified with said dataset of concentration values, or desorption rates, and characterizing the compared hydrocarbon fuel.

22. The method of claim 2 wherein temperature of the water is measured and the concentration measurements are further determined by correction for temperature variation from the system calibration.

23. The method of claim 19 wherein the temperatures of the water sample and the water are measured and the concentration measurements are further determined by correction for temperature variation from the system calibration.

* * * * *